US008518698B1

(12) United States Patent
Sugaya et al.

(10) Patent No.: US 8,518,698 B1
(45) Date of Patent: Aug. 27, 2013

(54) METHOD OF PROMOTING APOPTOSIS OF GLIOBLASTOMA TUMOR CELLS

(75) Inventors: Kimonobu Sugaya, Winter Park, FL (US); Stacey Mont, Maitland, FL (US); Angel Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 468 days.

(21) Appl. No.: 12/168,485

(22) Filed: Jul. 7, 2008

Related U.S. Application Data

(60) Provisional application No. 60/948,277, filed on Jul. 6, 2007.

(51) Int. Cl.
*C12N 5/074* (2010.01)
*C12N 5/00* (2006.01)
*C12N 5/02* (2006.01)
*A61K 48/00* (2006.01)

(52) U.S. Cl.
USPC .......... 435/378; 435/375; 424/83.2; 424/1.17

(58) Field of Classification Search
None
See application file for complete search history.

(56) References Cited

U.S. PATENT DOCUMENTS

2005/0019313 A1* 1/2005 Snyder et al. .............. 424/93.21
2006/0286117 A1* 12/2006 Fine et al. .................. 424/185.1

OTHER PUBLICATIONS

Kim et al. Clin. Cancer Res. Aug. 2005. 11(16) 5965-5970.*
Dwain et al. Current Stem Cell Research & Therapy, vol. 1, No. 1, Jan. 2006, pp. 79-84(6).*
Shimato et al.; Gene Therapy (2007) 14, 1132-1142.*
Yip, et al., Cancer J., 2003;9:189-204.*

* cited by examiner

*Primary Examiner* — Doug Schultz
(74) *Attorney, Agent, or Firm* — Timothy H. Van Dyke; Beusse, Wolter, Sanks, Mora & Maire, P.A.

(57) ABSTRACT

The invention provides a method of promoting apoptosis of human glioblastoma multiforme (GBM) tumor cells. The method comprises isolating GBM tumor cells from a human brain biopsy specimen, isolating human neural stem cells (HNSCs) from the biopsy specimen, transforming the isolated HNSCs with an operative PEX gene, and exposing GBM tumor cells to the transformed HNSCs to thereby promote apoptosis of the tumor cells mediated by the expressed PEX gene.

4 Claims, 4 Drawing Sheets
(4 of 4 Drawing Sheet(s) Filed in Color)

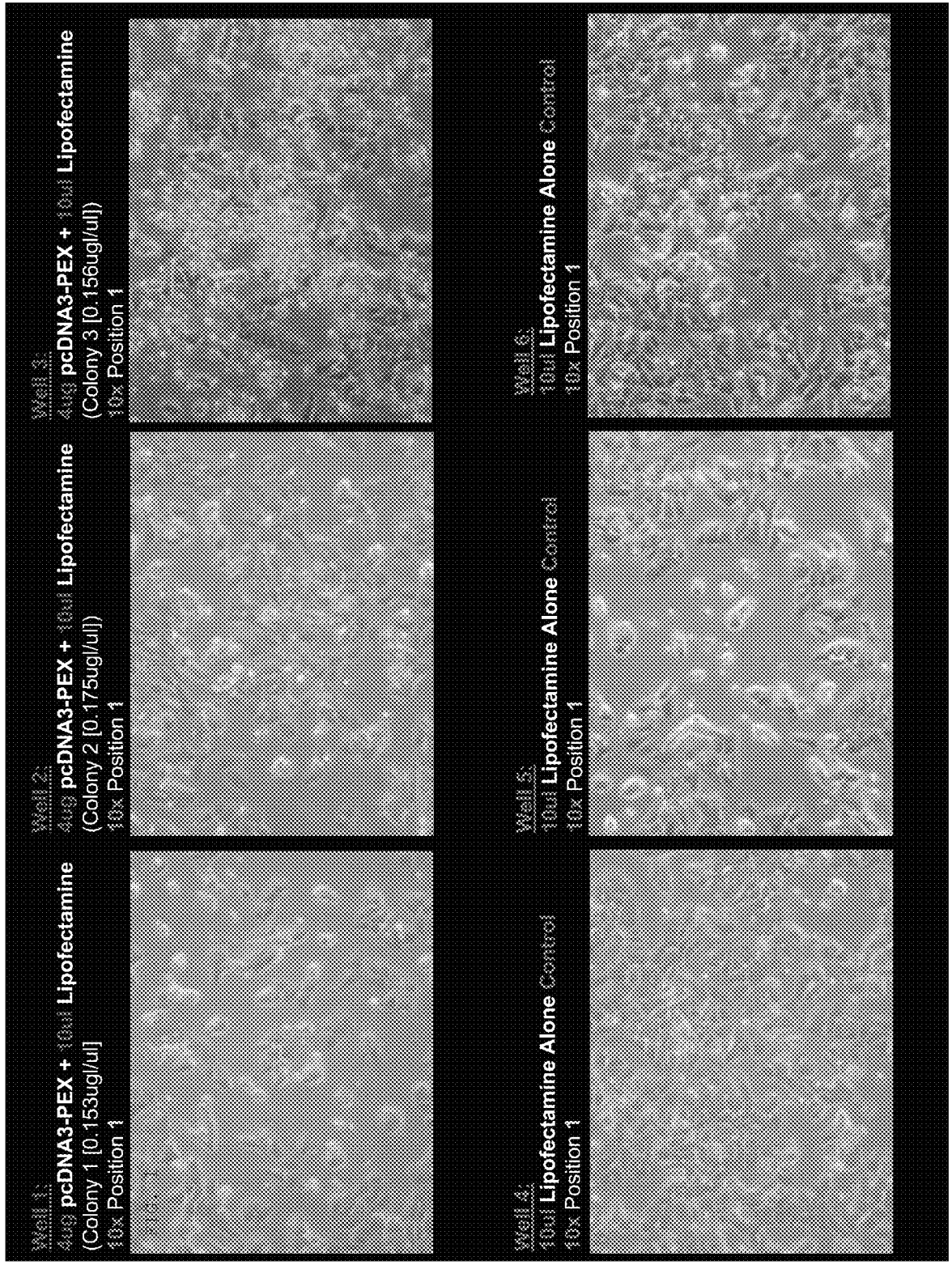

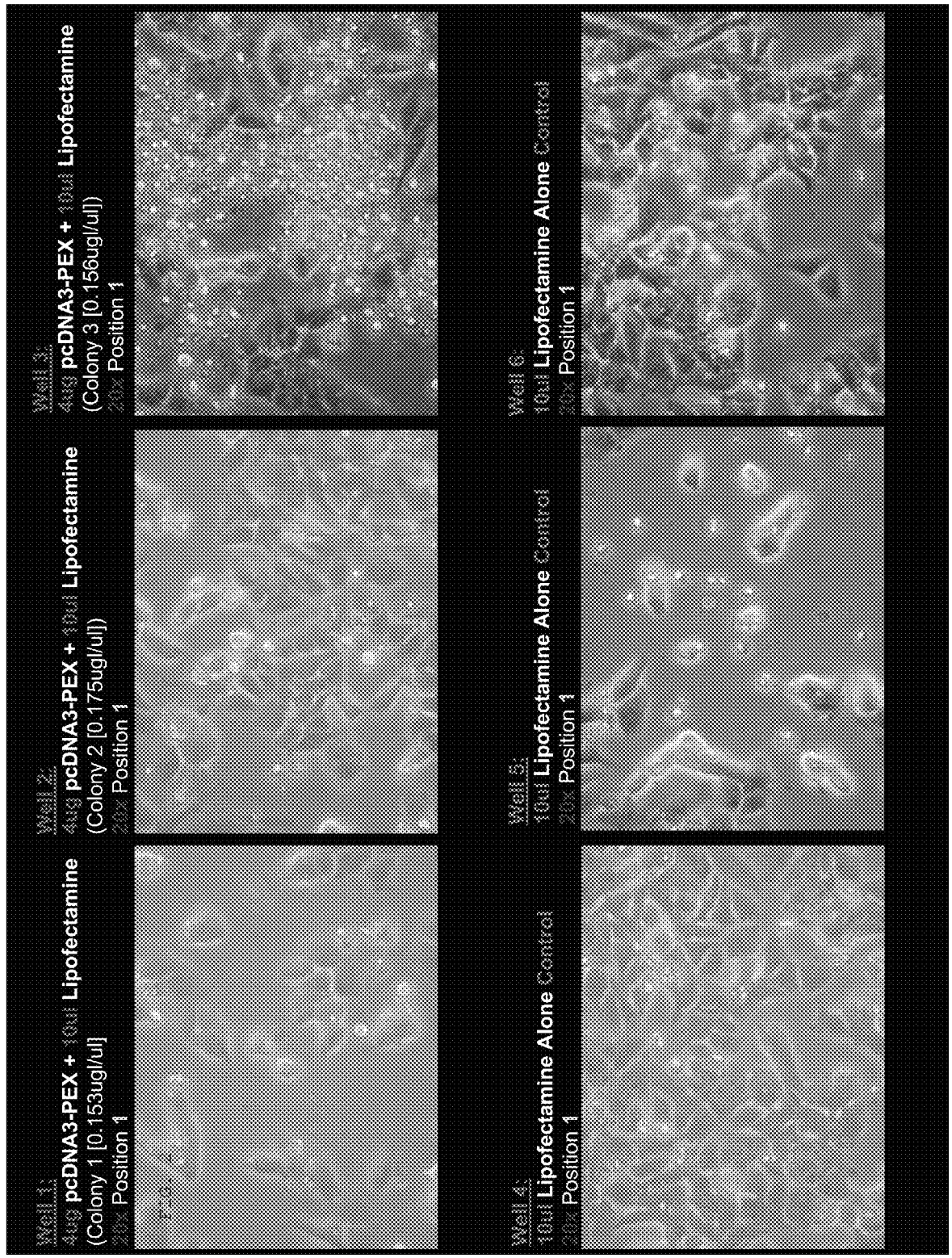

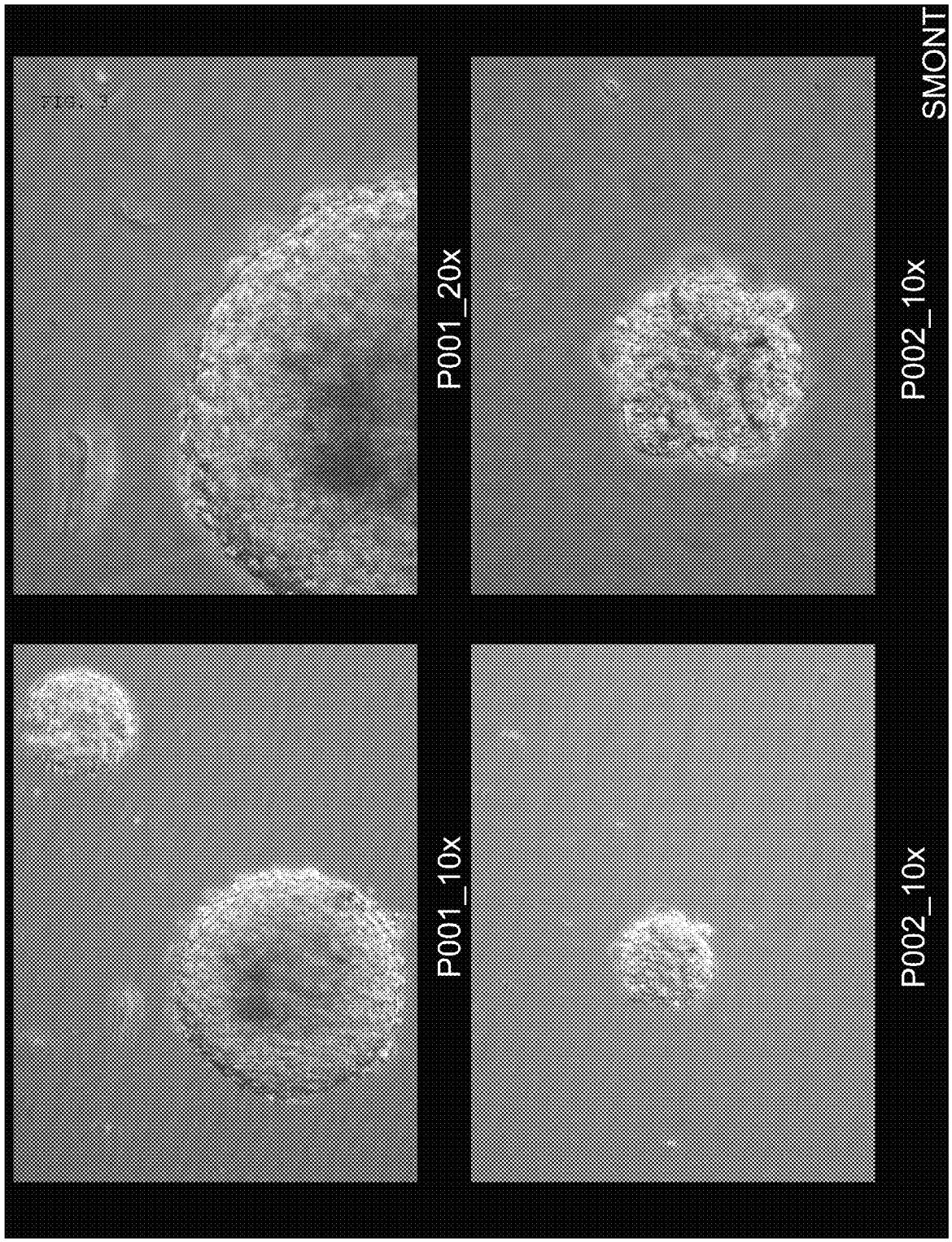

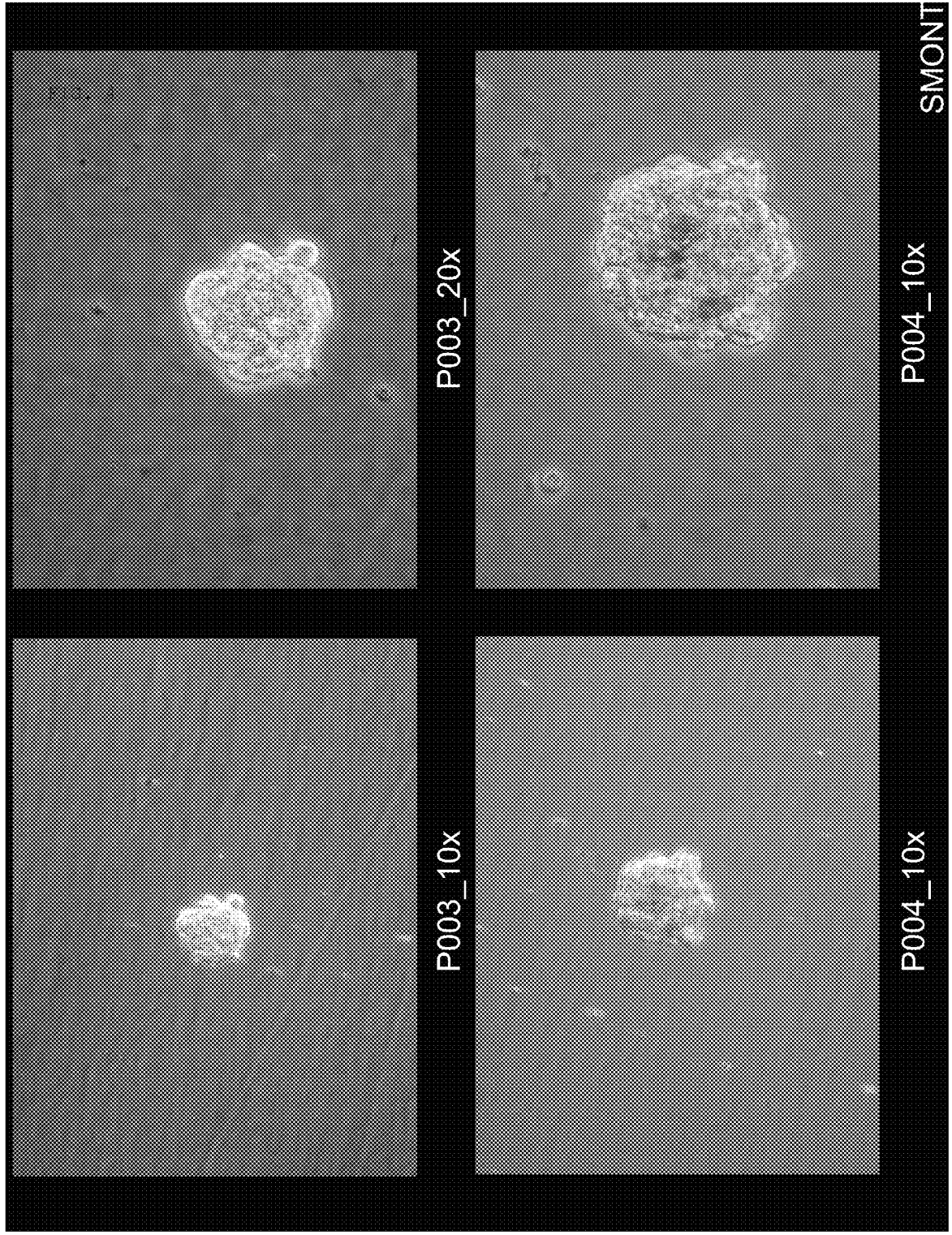

ND OF PROMOTING APOPTOSIS OF
METHOD OF PROMOTING APOPTOSIS OF GLIOBLASTOMA TUMOR CELLS

RELATED APPLICATION

This application claims priority from provisional application Ser. No. 60/948,277, which was filed on 6 Jul. 2007, and which is incorporated herein by reference in its entirety.

FIELD OF THE INVENTION

The present invention relates to the field of brain cancer and, more particularly, to a treatment which promotes destruction of brain tumor cells.

BACKGROUND OF THE INVENTION

Patients diagnosed with Glioblastoma multiforme (GBM) only survive a median time of sixteen (16) months through extensive neurosurgery and chemotherapy along with radiation therapy. Research has demonstrated that within a timeframe of five (5) days HNSCs are able to migrate next to the brain tumors in mice. Therefore, it may be concluded that the tumor itself along with surrounding tissue should contain an abundant amount of HNSCs. Integrating this knowledge, a novel GBM therapy may be devised. The long range goal is to remove tumors from GBM patients, isolate the patient's Human Neural Stem Cells (HNSCs), transfect them with the PEX gene within a mammalian expression vector and then transplant the patients original HNSCs back into the brain. PEX is part of the C-terminal fragment of MMP2 metalloproteinase shown to prevent "normal biding to alpha-V/beta-3 and disrupts angiogenesis and tumor growth". The central hypothesis is that after transfection of the patients HNSCs with the PEX gene, the cells will migrate to the site of tumor cells, express PEX and inhibit tumor growth and possibly promote apoptosis. The objectives of this project would be to achieve the following aims: AIM 1. Optimize a highly effective method for selecting all three (3) types of cells from a brain tumor sample. (Cancer Stem Cells, GBM Tumor Cells, Human Neural Stem Cells) AIM 2. To determine whether human neural stem cells transfected with the PEX gene effectively kill the tumor cells in vitro. AIM 3. To investigate whether PEX transfected HNSCs eliminate human tumor cells in vivo through mouse models. Aim 4. Perform clinical tests to determine whether PEX transfected HNSCs eliminate tumor cells in the patient. This proposed research is innovative, because it focuses on isolating Human Neural Stem Cells directly from tumor patient samples and transfecting them with an anti-cancerous gene such as PEX. This research is expected to have the following outcomes: (1) Isolation of all three types of the cells from patients' brain tumor samples; (2) demonstration that PEX transfected HNSCs will effectively inhibit tumor growth in-vitro and in-vivo; and (3) demonstration of elimination of GBM in patients using their own HNSCs expressing PEX. This research is significant because it will provide a novel GBM therapy using the patient's own HNSCs.

A present challenge in the treatment of glioblastoma multiforme is the fact that patients diagnosed with this disease rarely undergo surgery which effectively removes all carcinoma cells from the site of the lesion. Therefore a solution to this problem may be devised through isolation of Human Neural Stem Cells in the patient's own tumor. Through this effort we can use the patients HNSCs as therapy for the patient thus eliminating any possible chance of immunorejection from the patient.

SUMMARY OF THE INVENTION

With the foregoing in mind, the present invention advantageously provides a method of promoting apoptosis in human glioblastoma multiforme tumor cells (GBMTCs) by treating them with PEX transformed HNSCs. The present invention provides one of the initial steps in development of an effective treatment of GBM through the use of the patient's own PEX gene transfected HNSCs.

The present invention provides a method of promoting apoptosis of human glioblastoma multiforme (GBM) tumor cells. The method comprises isolating GBM tumor cells from a human brain biopsy specimen and also isolating human neural stem cells (HNSCs) from the biopsy specimen. The method then calls for transforming the isolated HNSCs with a PEX gene. Following transformation, the method continues by contacting GBM tumor cells (GBMTCs) with the transformed HNSCs to thereby promote apoptosis of the tumor cells. Those skilled in the art will recognize that the method may be carried out in vitro, but also may be carried out in vivo.

BRIEF DESCRIPTION OF THE DRAWINGS

The application file contains at least one drawing executed in color. Copies of this patent or patent application publication with color drawing(s) will be provided by the Office upon request and payment of the necessary fee.

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 1 shows phase-contrast photomicrographs of the following: well 1 shows PEX transformed HNSCs cocultured with GBMTCs and well 4, below, is a control for well 1 with lipofectamine alone, which causes a slight level of apoptosisf; well 2 shows another colony of GBMTCs in coculture with transformed HNSCs, and well 5 shows its lipofectamine control; well 3, shows colony 3 GBMTCs cocultured with transformed HNSCs and well 6 shows its lipofectamine control;

FIG. 2 shows the same wells as shown in FIG. 1, but at a higher magnification;

FIG. 3 shows GBMTCs in process of apoptosis when cocultured with PEX transformed HNSCs, top left and right slides and bottom left and right slides are the same pictures at different magnifications; and FIG. 4 shows four photomicrographs similar to those of FIG. 3 but with different GBMTC populations.

DETAILED DESCRIPTION OF PREFERRED EMBODIMENTS

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control.

In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

The first aim of this experiment was to effectively isolate all three types of cells: Cancer Stem Cells, Tumor Cells and Human Neural Stem cells. In order to achieve the following, surface markers for each cell have been identified: Cancer Stem Cells: ABCG2, CD133 (Singh, Clarke et al. 2003; Singh, Hawkins et al. 2004; Mohan, Kandalam et al. 2006; Park, Selvarajah et al. 2007) Tumor Cells: Tenascin (Brack, Silacci et al. 2006; Silacci, Brack et al. 2006) Human Neural Stem Cells: MCM2, 2F7 epitope (Schubert, Coskun et al. 2000; Mohan, Kandalam et al. 2006). Therefore using antibodies for each surface marker, attached to magnetic beads, selection was carried out using tissue from human brain biopses. The mixture of cells and antibody was passed through a magnetic tube and selection for each type of cell was achieved. After separation, the cells were maintained in culture in order to determine their morphology so as to provide yet another level to determine correct isolation of each type of cell. As a method to screen the efficiency of the surface markers, paraffin embedded tumor tissue was obtained. These samples were tested against primary antibodies that bind to these specific surface markers along with secondary antibodies in order to ensure effective binding. Different secondary antibodies with different fluorescent tags were used to test the uniqueness of the surface markers proposed. We expected that this method, when optimized, would be an efficient way to select and categorize each type of cell from a GBM patient tumor sample.

After HNSCs wee isolated from patient tumor samples and maintained in culture for a period of time, they were transfected with the PEX gene according to the procedure shown below.

The appended figures illustrate apoptosis of the GBMTCs following coculture with PEX transfected HNSCs.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

Transfection Protocol—For NT2 pcDNA3-PEX
DNA : Lipotectamine
1:2.5
4 ug per DNA Sample
pcDNA3-PEX Colony 1 [0.153 ug/ul]×26.2 ul=4 ug
pcDNA3-PEX Colony 2 [0.175 ug/ul]×22.9 ul=4 ug
pcDNA3-PEX Colony 3 [0.156 ug/ul]×25.7 ul=4 ug
4 ug DNA: 10 ul Lipotectamine/Per Well
6 Well Plate Format:
X-1 X-2 X-3 X-1=Colony 1 X-2=Colony 2 X-3=Colony 3
X-4 X-5 X-6 Cntrls→X-4=Lipo Alone X-5=lipo Alone X-6=Lipo Alone
1. Mix DNA with 50 ul of Opti-MEM:
    X-1: (26.2 ul DNA+23.8 ul Opti-MEM) (A-1)
    X-2: (22.9 ul DNA+27.1 ul Opti-MEM) (A-2)
    X-3: (25.7 ul DNA+24.3 ul Opti-MEM) (A-3)
    X-4 through X-6: (50 ul of Opti-MEM Alone) (A-4, A-5, A-6)
2 Mix Lipofectamine before using.
3. Add Lipofeciamine in 50 ul of Opti-MEM. (10 ul Lipofectamine 40 ul of Opti-MEM) (B-1, B-2, B-3) Also: (B-4, B-5, B-6)
4. Incubate this solution for 5 minutes at RT. Proceed to next step within 25 minutes.
5. After 5 minutes mix A·B (total volume: 100 ul). (A1+B1), (A2+B2), (A3+B3), (A4+B4), (A5+B5), (A6+B6)
6. Mix this solution gently and incubate for 20 minutes of RT (solution may appear cloudy)
7. Add the 100 ul DNA, Lipofectamine Complex to the each well of the 6 well plate with cells and medium and mix gently by rocking back and forth.
8. Incubate cells at 37° C. for 18-48 hours prior to testing for transgene expression
9. Medium may be changed after 4-6 hours.

That which is claimed:

1. A method of promoting apoptosis of human glioblastoma multiforme (GBM) tumor cells, the method comprising:
    obtaining a diseased human brain biopsy specimen comprising human GBM tumor cells and normal autologous human neural stem cells (HNSCs);
    isolating the normal autologous HNSCs from the diseased human brain biopsy specimen from the GBM tumor cells by use of a specific cell marker;
    transforming the isolated normal autologous HNSCs with an operative PEX gene; and
    exposing GBM tumor cells to the transformed normal autologous HNSCs to thereby promote apoptosis of the tumor cells mediated by the expressed PEX gene.

2. The method of claim 1 wherein contacting exposing is effected in vitro.

3. The method of claim 1 wherein contacting exposing is effected in vivo.

4. A method of producing transformed human neural stem cells (NHSCs), the method comprising:
    obtaining a diseased human brain biopsy specimen comprising human GBM tumor cells and normal autologous human neural stem cells (HNSCs);
    isolating the normal autologous HNSCs from the diseased human brain biopsy specimen from the GBM tumor cells by use of a specific cell marker; and
    transforming the isolated normal autologous HNSCs with an operative PEX gene.

* * * * *